United States Patent [19]

Coward

[11] Patent Number: 4,628,090
[45] Date of Patent: Dec. 9, 1986

[54] FLUORINE-CONTAINING ANTIFOLATES INCAPABLE OF POLYGLUTANAYTE FORMATION RELATED COMPOUNDS

[75] Inventor: James K. Coward, Troy, N.Y.

[73] Assignee: Rensselaer Polytechnic Institute, Troy, N.Y.

[21] Appl. No.: 767,122

[22] Filed: Aug. 19, 1985

Related U.S. Application Data

[63] Continuation-in-part of Ser. No. 642,808, Aug. 21, 1984, Pat. No. 4,584,375.

[51] Int. Cl.$^4$ ........................................... C07D 475/08
[52] U.S. Cl. .................................... 544/258; 544/260
[58] Field of Search ............................. 544/258, 260

[56] References Cited

U.S. PATENT DOCUMENTS 2,741,608  4/1956  Shive ..................................... 544/258
4,374,987  2/1983  Singh .................................... 544/260

OTHER PUBLICATIONS

McGuire, "Chemical and Engineering News", 62(28), p. 76, (7/9/84).
Burde, "Puti Sim. Izyskaniya Protivoopukholevykh Prep. 1968, 99, pp. 1033–1037.
Bergemann, "Synthesis (1), pp. 44–46 (1973).

Primary Examiner—Sidney Marantz
Assistant Examiner—Robert Benson
Attorney, Agent, or Firm—McGlew and Tuttle

[57] ABSTRACT

A methotrexate derivative having the following general formula is incapable of forming polyglutamate and thus is expected to have reduced cytotoxicity associated with the formation of polyglutamate derivatives in a living cell,

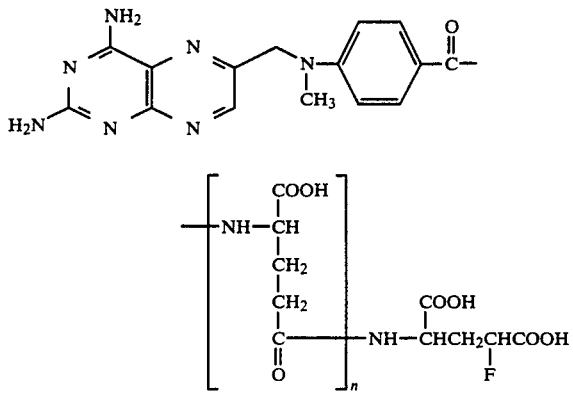

wherein n is from 0 to 5.

2 Claims, No Drawings

FLUORINE-CONTAINING ANTIFOLATES INCAPABLE OF POLYGLUTANAYTE FORMATION RELATED COMPOUNDS

STATEMENT OF GOVERNMENT INTEREST

The present invention resulted from research supported by the U.S. Public Health Service Department of Health and Human Services under PHS Grant No. 5 RO1 CA28097.

CROSS-REFERENCE TO RELATED APPLICATION

This is a continuation-in-part of co-pending parent application Ser. No. 642,808 filed Aug. 21, 1984, now U.S. Pat. No. 4,584,375.

FIELD AND BACKGROUND OF THE INVENTION

The present invention relates in general to methotrexate derivatives and in particular to such derivatives which are incapable of forming polyglutamates thus having reduced cytotoxicity.

Methods are known for preparing methotrexate and similar compounds. See for example, U.S. Pat. Nos. 4,080,325 to Ellard, 4,224,446 to Catalucci and 3,989,703 to Niculescu-Duvaz et al. Synthesis of similar compounds are also disclosed in U.S. Pat. Nos. 4,077,957 to Piper et al and 2,742,468 to Brockman et al.

Of particular interest in this field is U.S. Pat. No. 4,374,987 to Singh et al which discloses a process for preparing highly pure methotrexate.

Methotrexate is widely used in cancer chemotherapy as an antifolate. The chemical is toxic to normal cells however, as well as to malignant cells. One hypothesis is that this general cytotoxicity is due to the formation of polyglutamate derivatives of the drug once it is inside the cell. Since these polyglutamate derivatives do not leave the cell as rapidly as the parent drug, the drug is in effect "trapped" in the cell. This results in the death of the cell and the observed general cytotoxicity.

Methotrexate (MTX) was first observed to produce temporary remission in leukemia in 1948. See an article by Farber etal in the New England Journal of Medicine, 238:787–792 (1948). As noted above, it has since been widely used to treat various neoplasms. The general mode of action for MTX is understood. MTX acts as a repressor of cellular growth by initiating a chain of events which ultimately leads to inhibition of thymidylate synthesis. Thymidylate synthesis is a crucial step in DNA biosynthesis. MTX acts by inhibiting dihydrofolate reductase (DHFR), an enzyme necessary for the reduction of dihydrofolate to tetrahydrofolate. Tetrahydrofolate is an essential cofactor which is able to acquire a methylene group from serine. Thymidylate synthase can then transfer this one carbon unit from $N^5$, $N^{10}$-$CH_2$-tetrahydrofolate to 2′-deoxyuridine monophophate to generate thymidylate. In order for this reductive methylation to occur, functional DHFR must be coupled to a functional thymidylate synthase. This coupling is accomplished with the reduced forms of folic acid. MTX acts as a folate analogue which inhibits DHFR and uncouples it from thymidylate synthase. Rapidly proliferating cells, such as leukemias, are therefore most susceptable to MTX because of their accelerated DNA synthesis.

MTX has limited clinical value because of its cytotoxicity. When MTX is administered for leukemia chemotherapy, it is absorbed by normal host cells as well as the neoplasm. This causes inhibition of DHFR in normal as well as neoplastic cells. With high dosages of MTX, the normal host cells must be "rescued" by administering leucovorin. This is a derivative of tetrhydrofolate that can circumvent the inhibition of DHFR.

The cytotoxicity of MTX, is in turn believed to be related to the retention of polyglutamylated forms of MTX within the cells. It has been shown that polyglutamylated forms of MTX still capable of DHFR inhibition, leave the cells much less rapidly than unmetabolized (non-polyglutamylated) MTX.

Polyglutamate formation is a well established means by which cells modify folates in order to retain them. See an article in Archives of Biochemistry and Biophysics, Vol. 216, No. 2, July, pages 466–476, 1982, by Balinska et al.

SUMMARY OF THE INVENTION

The present invention is drawn to a new methotrexate derivative and the synthesis thereof, wherein the methotrexate derivative has the general formula:

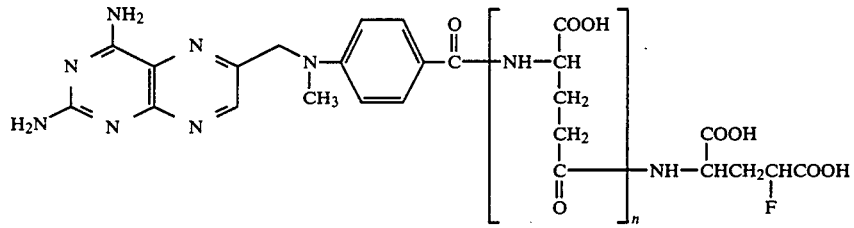

where n is from 0 to 5.

This new methotrexate derivative contains in its structure atoms which prevent the formation of polyglutamates. The compound may thus show less general cytotoxicity when used in chemotherapy.

The new methotrexate derivative might also have applications for treatment of certain skin diseases such as psoriasis, or treatment of arthritis.

Further experimentation must be conducted however, since undesirable side effects might be present which are not associated with polyglutamate formation.

The methotrexate derivative of the invention, where n=0, and shown below as (A), is different from the prior art in the inclusion of the fluorine atom at the carbon atom #4 (γ) of the glutamic acid function. Where n=1 through 5, the new derivative includes additional glutamic acid residues between the fluorine-containing glutamate and the p-aminobenzoic acid function.

A particularly advantageous compound shown below and labelled (B) is a fluorinated derivative of 5-formyltetrahydrofolate (leucovorin). Prior art derivatives of similar type are currently used in "high-dose methoxtrexate" cancer chemotherapy. Compound (B) could have interesting biological properties when used in conjunction with either methotrexate or the general formula of the present inventive methotrexate derivatives.

Another compound of interest shown at (C) may act as a "depot" form of the fluorinated methotrexate (A) of the general form set forth in this application. As such it might be useful as an alternative to the parent compound.

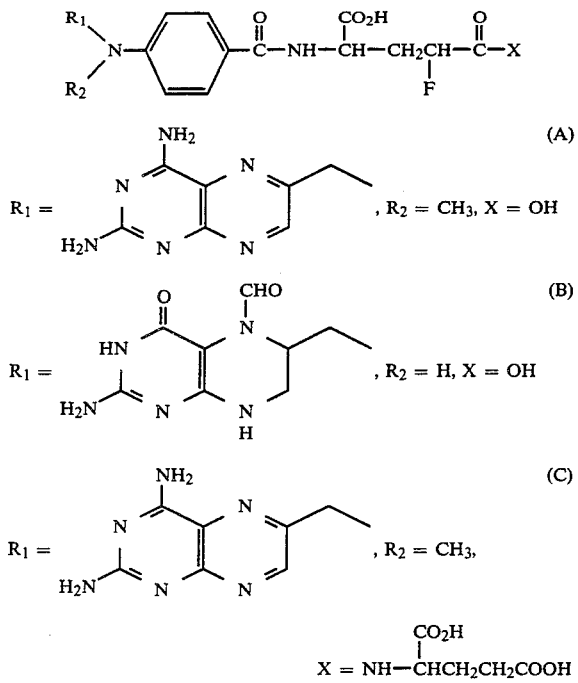

A more general formula for the inventive compound which encompasses the formulas (B) and (C) as well as γ-fluoremethotrexate, a variant of the general equation wherein n is equal to 0, is set forth above. The γ-fluoremethotrexate is indicated as (A).

MTX analogs have been found with some ability to resist polyglutamylation. See for example Rosowsky et al *J. Med. Chem.*, 26:1719 (1983) and Rosowsky et al *Biochemical Pharm.*, 33(1): 155-161 (1984). These compounds have been reported to have affinity for DHFR compatible to MTX and also to be poor substrates for FPGS (folylpolyglutamate synthetase).

Rosowsky et al has also reported a compound where the glumate portion of MTX is replaced by DL-homocysteic acid. This compound is shown to tightly bind DHFR and appears to weakly inhibit FPGS, making it the first compound reported to inhibit both these mammalian enzymes.

The present invention for the first time presents a fluorinated compound, e.g. D,L-threo-4-fluoroglutamic acid which inhibits FPGS. It is proposed that by replacing the glutamate moiety of MTX with 4-fluoroglutamate, as in the present invention, the new MTX analog becomes capable of inhibiting DHFR and incapable of acting as a substrate for FPGS.

The synthesis of 4-amino-10-methyl-pteroyl-4-fluoroglutamic acid (fluoromethotrexate or FMTX) follows.

Activity of the particular FMTX whose synthesis follows has been confirmed by in vitro experiments as will be discussed later.

DETAILED DESCRIPTION OF THE INVENTION

Synthesis of the above FMTX was accomplished as shown in Equation 1. First, protection of the α- and γ-carboxyl functions of D,L-erythro, threo-4-fluoroglutamic acid (2) was carried out using standard tert-butylation procedures. D,L-4-fluoroglutamic acid was obtained as a 1:1 mixture of the erythro:threo isomers from Calbiochem. This protection involved stirring 2 in liquid isobutylene accompanied by a catalytic amount of concentrated $H_2SO_4$ in a pressure bottle for four days. After, work-up 3 was obtained in a 72% yield.

Reaction of 3 with p-(carbobenzyloxymethylamino)-benzoyl chloride proceeded smoothly to give 4. This method entailed adding freshly prepared acid chloride to a solution of 3 in a biphasic $EtOAc/NaHCO_3$ (aq) system. The resulting amide 4, was obtained in 93% yield (See Tang et al, *J. Org. Chem.*, 48:5001 (1983).

Hydrogenation of 4 to remove the carbobenzyloxy group was run in neutral methanolic solution using 10% Pd on carbon catalyst. The yield of the deprotected material, 5, was 92%.

Coupling of the glutamate, 5 to the pterin heterocycle was carried out using the procedure of Piper and Montgomery (*J. Org. Chem.*, 42(2):208 (1977)). In this procedure, 5 was dissolved in $Me_2NAc$, followed by the addition of 2,4-Diaminopteridine-6-bromomethyl hydrobromide (see the above Tang et al article).

EQUATION 1

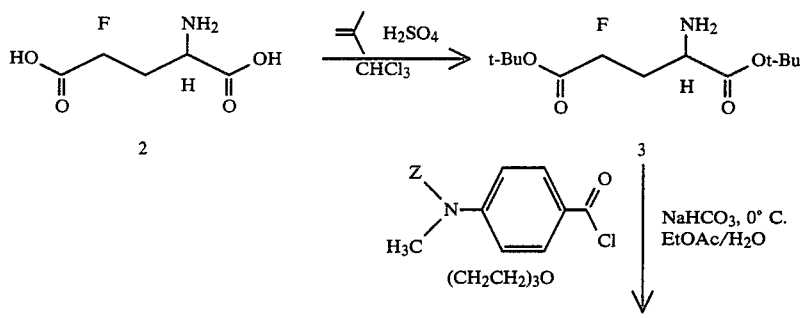

EQUATION 1

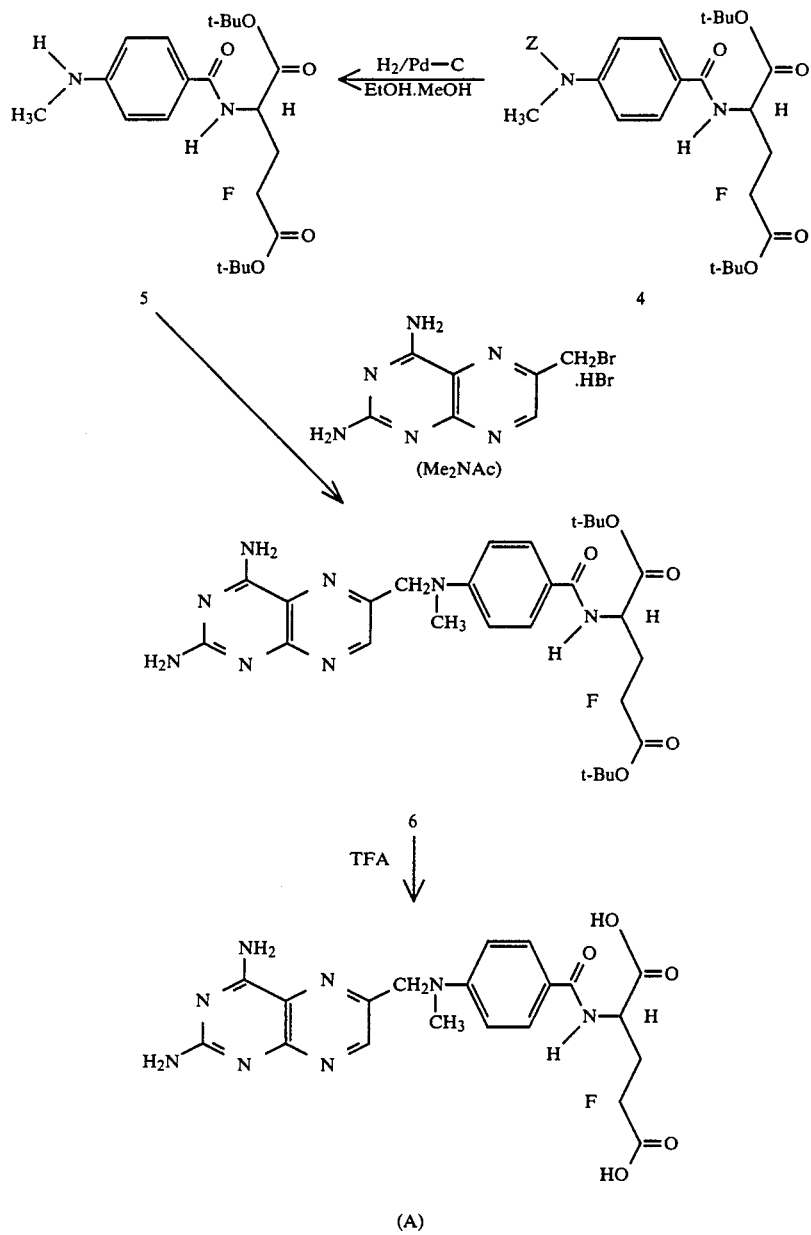

(A)

The mixture was allowed to stir at 50°–55° C. for four hours, after which the solvent was removed in vacuo. The resulting crude 6 was treated with trifluoroacetic acid to remove the tert-butyl groups.

The crude FMTX (A) was purified on a DEAE cellulose column using a linear NH$_4$HCO$_3$ gradient (0.015M to 0.6M). The amount of product recovered from 5 through the DEAE cellulose purification was 33%. The yield over five steps and purification was 24%.

Chromatographic analysis (TLC, HPLC) of FMTX indicated it to be homogeneous material. The UV absorbance spectrum of FMTX is characteristic of MTX, as one might expect.

$^{19}$F NMR exhibits two $^{19}$F resonances at pH=1. This splitting of the $^{19}$F peak is a result of both D,L threo and D,L erythro isomers being present. The multiplicity of each resonance is seven and can be explained by Table 1.

TABLE 1

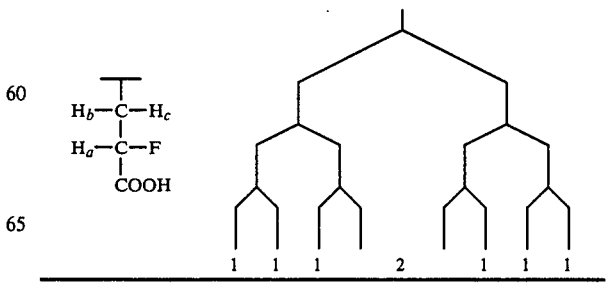

As shown in Table 1 fluorine absorption is split by Ha into a doublet and the doublet is split by Hb into a quartet. This quartet should then be split to give an octet under the influence of Hc, however, the barricenter lines coincide giving the observed septet (See Bergmann et al, Synthesis, 44 (1973). At pH=6 a single $^{19}$F resonance is seen with a multiplicity of fourteen. It thus appears that the two separate diastereomeric $^{19}$F resonances coalesce near neutral pH.

Proton NMR studies of FMTX reveal that the proton resonance belonging to the hydrogen geminal to fluorine is shifted downfield ($\delta$ 5.42) as one would expect. The multiplicity of this proton was not well resolved in the FMTX spectrum, but $^1$H NMR studies with 4-fluoroglutamic acid esters allowed the signal to be discerned as a doublet of quartets. This multiplicity can be rationalized to some extent using the same reasoning that was presented for the fluorine resonance.

Turning now to the activity of FMTX, FMTX has been shown to retain the potent inhibitory activity of MTX against DHFR. Also FMTX is not a substrate for the rat liver FPGS (on which in vitro tests were run) and shows toxicity levels several thousand times lower than MTX when studied in long term pulse administration experiments using cultured hepatic cells. Table 2 shows the path taken by folates and antifolates when incubated with FPGS, ATP, and glutamic acid. Table 2 also shows the inhibition mechanism of FMTX, the present invention where X=F.

Table 3 shows the biochemical basis for the present invention; i.e. chain termination of the FPGS reaction by the alternate substrate, D,L-threo-4-fluoroglutamic acid (See McGuire and Coward, J. Biol. Chem. 260, 6747 (1985)).

Uptake of FMTX by hepatic cells is nearly identical in terms of rate and extent as unmetabolized MTX. Similarly, the efflux (transport out) of FMTX from hepatic-cells occurs at a rate which is essentially identical to unmetabolized MTX. The major difference is that the cells given MTX contain large amounts (60%-90%) of MTX polyglutamate derivatives which efflux only very slowly, and thus are trapped in the cell. In contrast, cells given MFTX contain less than 5% of the analgous FMTX polyglutamates. The recent experiments have also demonstrated that the biosynthesis of thymidyate, and therefore DNA synthesis, is only very weakly affected in the pulse administration experiments mentioned above. This correlates well with the marked decrease in cytotoxicity under the pulse conditions, and supports the hypothesis that the inability of FMTX to form polyglutamate derivatives is the basis for the observed biological effects.

TABLE 2

REACTION CATALYZED BY
FOLYLPOLYGLUTAMATE SYNTHETASE

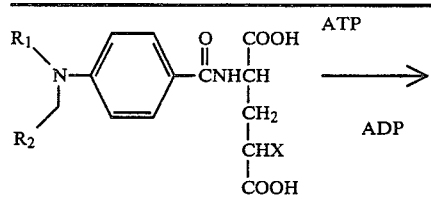

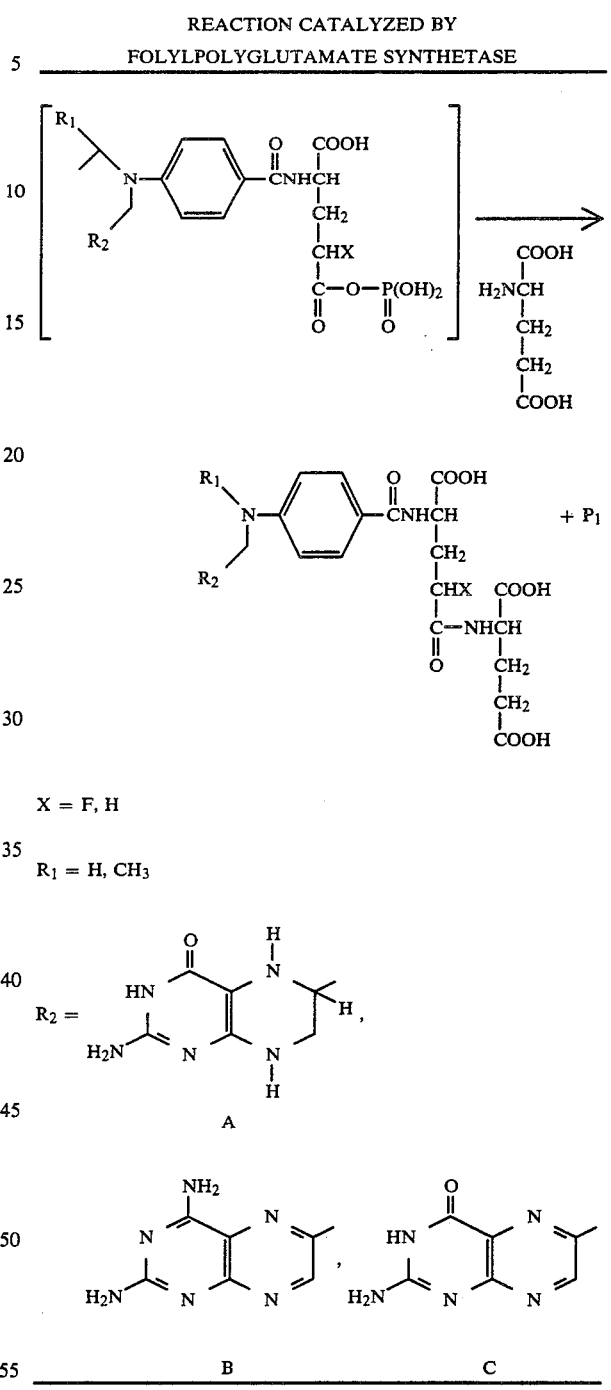

Tetrahydrofolate = X = H, $R_1$ = H, $R_2$ = A (undergoes polyglutamylation)
Folic Acid = X = H, $R_1$ = H, $R_2$ = C (undergoes polyglutamylation
Methotrexate = X = H, $R_1$ = CH$_3$, $R_2$ = B (undergoes polyglutaylation)
Fluoromethotrexate = X = F, $R_1$ = CH$_3$, $R_2$ = B (resists polyglutamylation)

The preliminary biochemistry shows that FMTX inhibitions of DHFR is comparable to MTX without being nearly as toxic to cells. Hopefully, the potential for this new compound as a treatment for leukemia will be exploited further.

TABLE 3
REACTION CATALYZED BY FOLYLPOLYGLUTAMATE SYNTHETASE

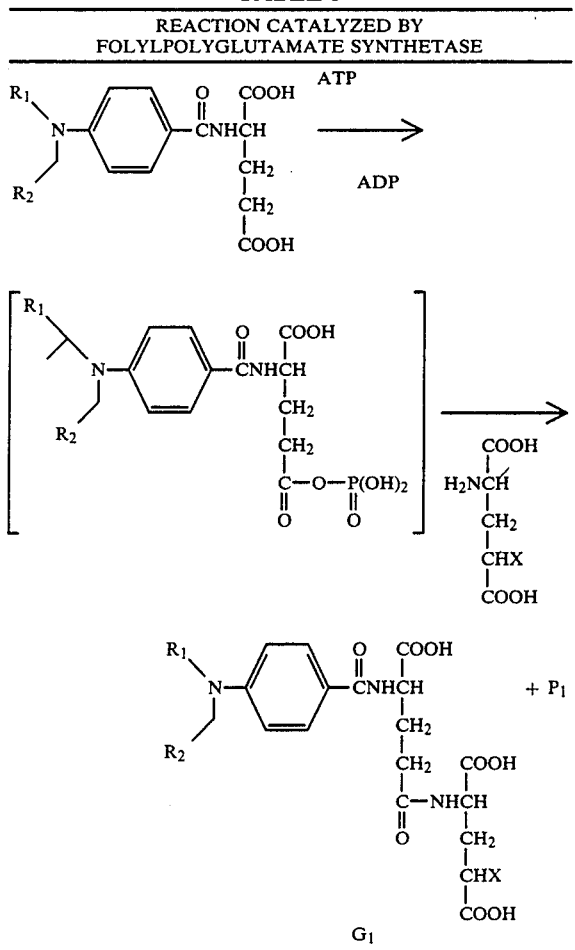

X = F, H
R₁ = H, CH₃

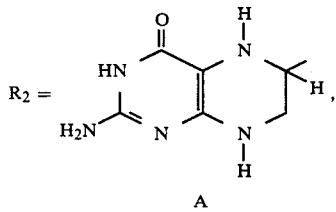

TABLE 3-continued
REACTION CATALYZED BY FOLYLPOLYGLUTAMATE SYNTHETASE

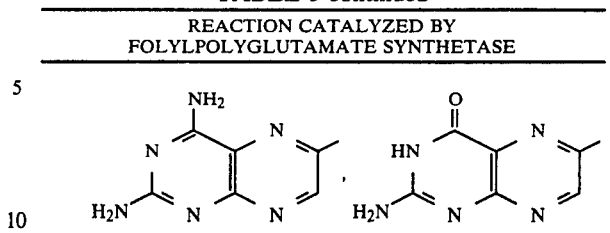

B                C

Tetrahydrofolate = $R_1$ = H, $R_2$ = A
Folic Acid = $R_1$ = H, $R_2$ = C
Methotrexate = $R_1$ = $CH_3$, $R_2$ = B
Glutamic Acid = X = H
4-Fluoroglutamic acid = X = F
$G_1$ can undergo further polyglutamylation for all $R_1$ and $R_2$ derivatives when X = H.
$G_1$ can not undergo further polyglutamylation for any $R_1$ and $R_2$ derivatives when X = P.

The following discussion details the synthesis of the $G_1$ derivative of MTX (Table 3, X=F) prepared using an approach similar to that already described for the synthesis of FMTX.

Equation 2 shows the synthetic steps involved in the construction of the required N-[p methyl-aminobenzoyl]-glutamyl-γ-4-fluoroglutamic acid (12). The free acid 7 was obtained by treatment with Dowex 50WX8 in 60% EtOH/H₂O. Coupling of the α, γ-carboxyl protected D,L-erythro, threo-4-fluoroglutamate ester to 8 was accomplished using DCC/HOBt giving the pipeptide 9 in 90% yield, hydrogenation of 9 in MeOH using 10% Pd on carbon catalyst gave the free amine 10 in quantitative yield.

The coupling of 10 to p-(carbobenzyloxymethylamino)benzoyl chloride to give 11, followed by hydrogenolysis to give 12, was carried out as described for the synthesis of 5 (equation 1). Coupling of the dipeptide, 12, to the pterin heterocycle, deblocking with TFA, and purification of the desired product (I, n=1) on DEAE cellulose was also carried out as described for the synthesis of 5 (equation 1).

EQUATION 2

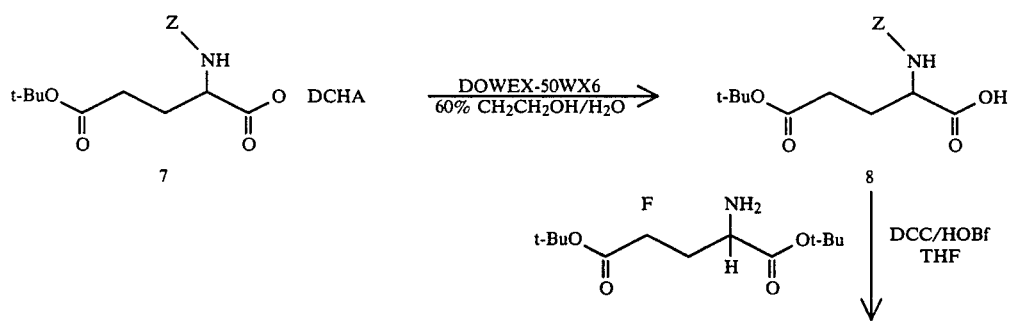

-continued
EQUATION 2

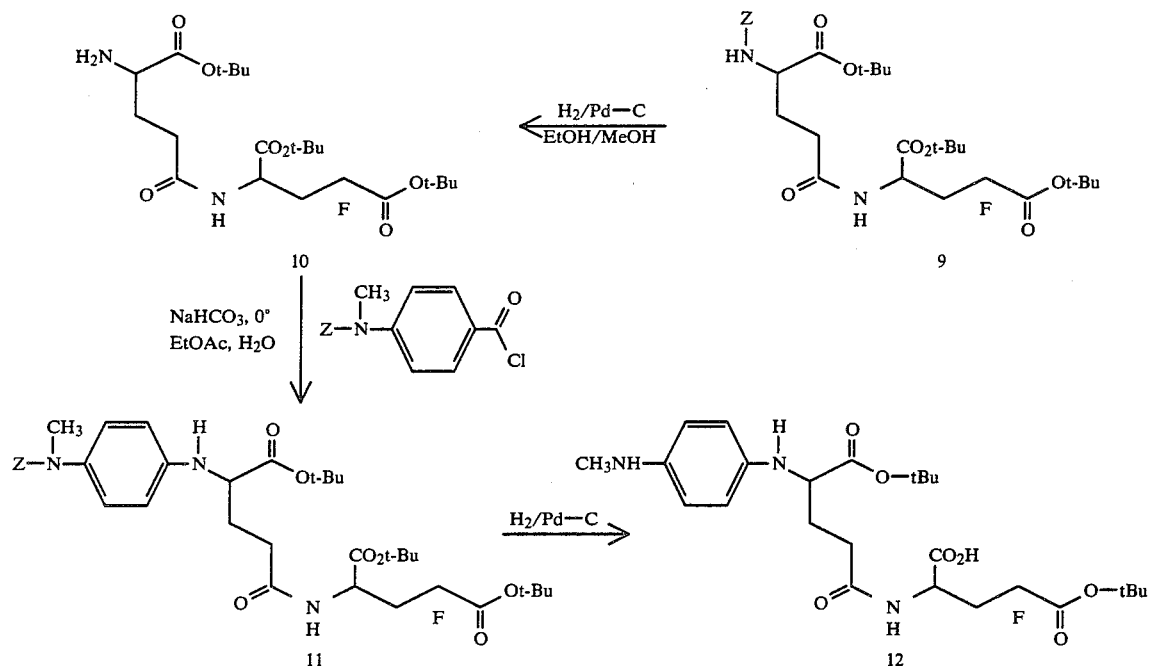

As regards compound (B), which is the γ-fluorinated derivative of 5-formyltetrahydrofolate (leucovorin), this is prepared in corresponding manner such that the 5-formyl group inherently functions in the same manner to protect the reduced pteridine ring which is otherwise labile to oxidation, while acquiring a methylene group from serine for eventually generating thymidylate. The difference is that compound (B) is inherently incapable of undergoing polyglutamylation as normally occurs with 5-formyltetrahydrofolate in the cell, yet like the latter, inherently acts to "rescue" the cell from the cytotoxic effects of MTX when administered for this antidote purpose. Compound B can inhibit continued synthesis of MTX polyglutamates, while not itself being an FPGS enzyme substrate, eventually becoming γ-fluorotetrahydrofolic acid instead of tetrahydrofolic acid as occurs with 5-formyltetrahydrofolate.

Thus, compound (B), which may be termed γ-fluoroleucovorin, γ-fluoro folinic acid, or 5-formyl tetrahydro-γ-fluorofolic acid (ketol form), i.e. 5-formyl tetrahydro pteroyl-γ-fluroglutamic acid or more precisely N-[p-([2,4-diamino-6-pteridinyl)methyl]methylamino)benzolyl]-γ-fluoroglutamic acid, may thus be inherently used, as earlier noted, in conjunction either with methotrexate, as a non-substrate or non-polyglutamylatable antagonist or antidote therefor, or with the compounds of formula (1) above, i.e. FMTX (where n is 0) or its γ-fluoroglutamate end stopped or chain stopped polyglutamylated form (where n is 1 to 5), for concordant non-substrate purposes in enhancing the eventual production of γ-fluorotetrahydrofolic acid therefrom (like the production of tetrahydrofolic acid from leucovorin) in conjunction with the main chemotherapeutic action of the formula (1) compounds which perform the role of MTX without its cytotoxic production of otherwise slowly or poorly cell effluxed polyglutamates.

As regards compound (C), which is the monoglutamylated "depot" form of compound (A), i.e. 4-amino-10-methylpteroyl-γ-fluoroglutamyl glutamic acid or more precisely N-[p-([(2,4-diamino-6-pteridinyl)methyl]methylamino)benzoyl-N'-γ-fluoroglutamyl]-glutamic acid, this is inherently useable as an alternative to FMTX. Hence, when administered in place of FMTX, compound (C) is inherently acted upon in the cell by attendant γ-glutamyl hydrolase which hydrolyzes off the terminal glutamyl group to form FMTX in situ and glutamic acid, a normal cell constituent.

Thus, compound (C) inherently provides for sustained release incrementally in the cell of FMTX or compound (A) as the attendant γ-glutamyl hydrolase increasingly causes hydrolytic splitting off of the terminal glutamyl group from its "depot" compound (C) whereby to permit more versatile dosage administration in the contemplated cancer chemotherapy, e.g. in the case of leukemia.

Compound (C), in which the internal γ-fluoroglutamyl group is insulated by the terminal glutamyl group, when administered will pass through the body and at its site of action will be hydrolyzed in situ in the cell by γ-glutamyl hydrolase to the active form FMTX or compound (A), having the inherent advantage of being administerable in longer pulse dosage procedures than FMTX, or by continuous infusion, e.g. IV administration, yet ultimately being hydrolyzed in the cell to that active form, FMTX.

Compound (C) is thus a chemically synthesizable precursor of compound (A) which of course according to the present invention can be prepared by standard peptide coupling reactions as were utilized in the synthesis of compound (1) above where n equals 1. Like compound (A), its "depot" form compound (C) is similarly of less general toxicity than MTX when used in chemotherapy, whereas compound (B) is a beneficial antidote like leucovorin and is inherently an inhibitor of MTX polyglutamylation and thus is not cytotoxic.

While a specific embodiment of the invention has been shown and described in detail to illustrate the application of the principles of the invention, it will be understood that the invention may be embodied otherwise without departing from such principles.

What is claimed is:

1. A compound having the formula:

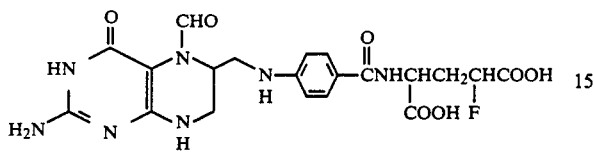

2. A compound having the formula;

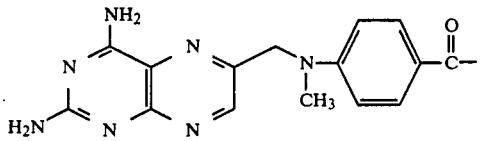

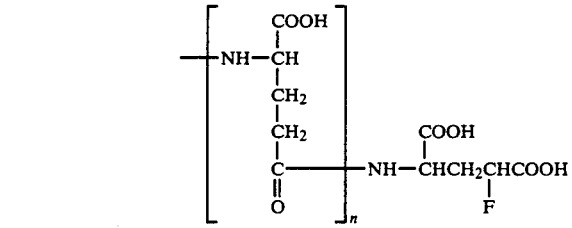

wherein n is from 1 to 5.

* * * * *